United States Patent
Woolaston et al.

(10) Patent No.: US 8,527,052 B2
(45) Date of Patent: Sep. 3, 2013

(54) THERMOELECTRIC POWER SUPPLY

(75) Inventors: Jesse Woolaston, Cremorne (AU); Dirk Fiedler, Elanora Heights (AU)

(73) Assignee: Cochlear Limited, Macquarie University, NSW (AU)

( * ) Notice: Subject to any disclaimer, the term of this patent is extended or adjusted under 35 U.S.C. 154(b) by 671 days.

(21) Appl. No.: 11/631,080

(22) PCT Filed: Jul. 12, 2005

(86) PCT No.: PCT/US2005/024541
§ 371 (c)(1),
(2), (4) Date: Nov. 7, 2008

(87) PCT Pub. No.: WO2006/017226
PCT Pub. Date: Feb. 16, 2006

(65) Prior Publication Data
US 2009/0182392 A1    Jul. 16, 2009

Related U.S. Application Data (60) Provisional application No. 60/586,718, filed on Jul. 12, 2004.

(51) Int. Cl.
*A61N 1/00* (2006.01)
*H01L 35/30* (2006.01)
(52) U.S. Cl.
USPC ............................................ 607/35; 136/205

(58) Field of Classification Search
USPC .................................. 607/35, 57, 37; 136/205
See application file for complete search history.

(56) References Cited

U.S. PATENT DOCUMENTS

| | | | |
|---|---|---|---|
| 3,384,806 A | | 5/1968 | Hartman |
| 5,419,780 A | * | 5/1995 | Suski ............................. 136/205 |
| 6,131,581 A | | 10/2000 | Leysieffer et al. |
| 6,212,431 B1 | * | 4/2001 | Hahn et al. ....................... 607/61 |
| 6,470,212 B1 | | 10/2002 | Weijand et al. |
| 6,640,137 B2 | | 10/2003 | MacDonald |
| 2003/0125604 A1 | * | 7/2003 | Kochamba et al. .............. 600/37 |
| 2003/0176900 A1 | * | 9/2003 | MacDonald .................... 607/61 |

OTHER PUBLICATIONS

International Search Report. PCT/US05/24541, filed Jul. 12, 2005. Mailed Nov. 15, 2005.

\* cited by examiner

*Primary Examiner* — Christopher D Koharski
*Assistant Examiner* — Catherine Voorhees
(74) *Attorney, Agent, or Firm* — Kilpatrick, Townsend & Stockton, LLP.

(57) ABSTRACT

A thermoelectric power source for generating power for use by at least one load device including an implantable thermoelectric unit having at least one thermoelectric device configured to be electrically coupled to the at least one load device, and at least one impedance matching device constructed and arranged to match an output impedance of the thermoelectric device with an input impedance of the load device.

30 Claims, 8 Drawing Sheets

THERMOELECTRIC POWER SUPPLY

CROSS-REFERENCE TO RELATED APPLICATIONS

This application is a national stage application under 35 USC §371(c) of PCT Application No. PCT/US2005/024541, entitled "Thermoelectric Power Supply," filed on Jul. 15, 2005, which claims the priority of U.S. Provisional Patent No. 60/586,718 entitled, "Optimization of Thermoelectric Devices For Powering Active Implantable Medical Devices," filed Jul. 12, 2004. The entire disclosure and contents of the above applications are hereby incorporated by reference herein.

The present application makes reference to the following patents and patent applications: U.S. Pat. Nos. 4,532,930, 5,758,651, 6,131,581, 6,470,212, 6,537,200, 6,565,503, 6,575,894, 6,640,137 and 6,697,674, and, WO 2002/082982 and WO 2004/021885, all of which are hereby incorporated by reference herein in their entirety.

BACKGROUND

1. Field of the Invention

The present invention relates generally to power supplies and, more particularly, to thermoelectric power supplies.

2. Related Art

Medical devices which are partially or completely implanted in a patient often require power to perform various therapeutic or diagnostic operations. Such power-consuming medical devices, commonly referred to as active implantable medical devices, or AIMDs, obtain the requisite power from a variety of power sources. Conventional power sources include, for example, implanted non-rechargeable and rechargeable batteries, an external energy storage device operatively connected to the implanted device via a percutaneous lead or a transcutaneous transfer system, electrochemical elements, biofuel cells, nuclear batteries and devices for direct conversion of the mechanical energy of motion into electric power by means of mechanical-electrical converter principles, mechanical micro-variation systems and the like. Such conventional approaches have a variety of associated drawbacks as described in U.S. Pat. Nos. 6,131,581, 6,470,212 and 6,640,137, which are hereby incorporated by reference herein in their entireties.

One power source of particular relevancy to the present invention is a thermoelectric device. Thermoelectric devices are very small, very light and completely silent solid state devices that can operate as a heat pump or as an electrical power generator with no moving parts. Thermoelectric devices such as Peltier effect-based thermoelectric power generators and Seebeck effect-based thermoelectric energy converters, act to directly convert the thermal energy of the body into electrical energy so as to provide an AIMD with electrical energy. U.S. Pat. No. 6,131,581, which is hereby incorporated by reference herein, shows a Seebeck effect-based thermoelectric device. This device functions by effectively harnessing the temperature difference between the core temperature of the body and the surface temperature of the body at the implantation site, or by harnessing temperature gradients within the body. This temperature difference, as a thermodynamic form of energy, is converted directly into electrical energy by the thermoelectric device. The Seebeck effect is achieved, for example, by the structural pairing of different metals which are spaced far apart in thermoelectric series. Even more efficient use of the Seebeck effect may be attained by the constructive connection of specially doped semiconductor materials as discussed in U.S. Pat. No. 6,131,581.

SUMMARY

In accordance with one aspect of the present invention, a thermoelectric power source for generating power for use by at least one load device is disclosed. The thermoelectric power source comprises: an implantable thermoelectric unit comprising at least one thermoelectric device configured to be electrically coupled to said at least one load device; and at least one impedance matching device constructed and arranged to match an output impedance of said thermoelectric device with an input impedance of said load device.

In accordance with another aspect of the present invention, a thermoelectric power source for generating power for use by at least one load device is disclosed. The power source comprises: an implantable thermoelectric unit comprising an array of a plurality of thermoelectric devices configured to be electrically coupled to said at least one load device; and a plurality of impedance matching devices constructed and arranged to match an output impedance of a group of one or more of said plurality of thermoelectric devices with an input impedance of said load device.

In accordance with a further aspect of the present invention, an active implantable medical device is disclosed. The device comprises: a power-consuming implantable component; and a thermoelectric power source for generating power for use by at least one load device comprising: an implantable thermoelectric unit comprising n array of a plurality of thermoelectric devices configured to be electrically coupled to said at least one load device; and a plurality of impedance matching devices constructed and arranged to match an output impedance of a group of one or more of said plurality of thermoelectric devices with an input impedance of said load device.

DETAILED DESCRIPTION

Aspects and embodiments of the present invention are directed to a thermoelectric power source which may be used to provide power to any load device now or later developed. For example, in certain applications, the load device may be an energy storage device such as a rechargeable battery or capacitors. In other applications, the load device may be a power-consuming device. While in other embodiments, the load device comprises a combination of energy storage and power consuming devices. Power-consuming and energy storage devices are generally and collectively referred to herein as load devices.

In certain applications described herein, embodiments of the thermoelectric power source are utilized to provide power to one or more components of an implantable medical device. Implantable medical devices which utilize power are commonly referred to as active implantable medical devices (AIMDs). AIMDs include partially- or completely-implantable medical devices configured to be implanted permanently or temporarily in a recipient (also referred to herein as a patient). Examples of AIMDs include but are not limited to implantable devices which provide stimulation to muscles and/or nerve fibers, devices which sense biological or related conditions, communication devices, drug deliver devices, devices which perform substitute or support functions for biological processes, systems or organs, such as cardiac assist devices, and other therapeutic or diagnostic devices. These and other active devices, and their components, are collectively and generally referred to herein as AIMDs, implantable devices, and the like.

Figure 1:
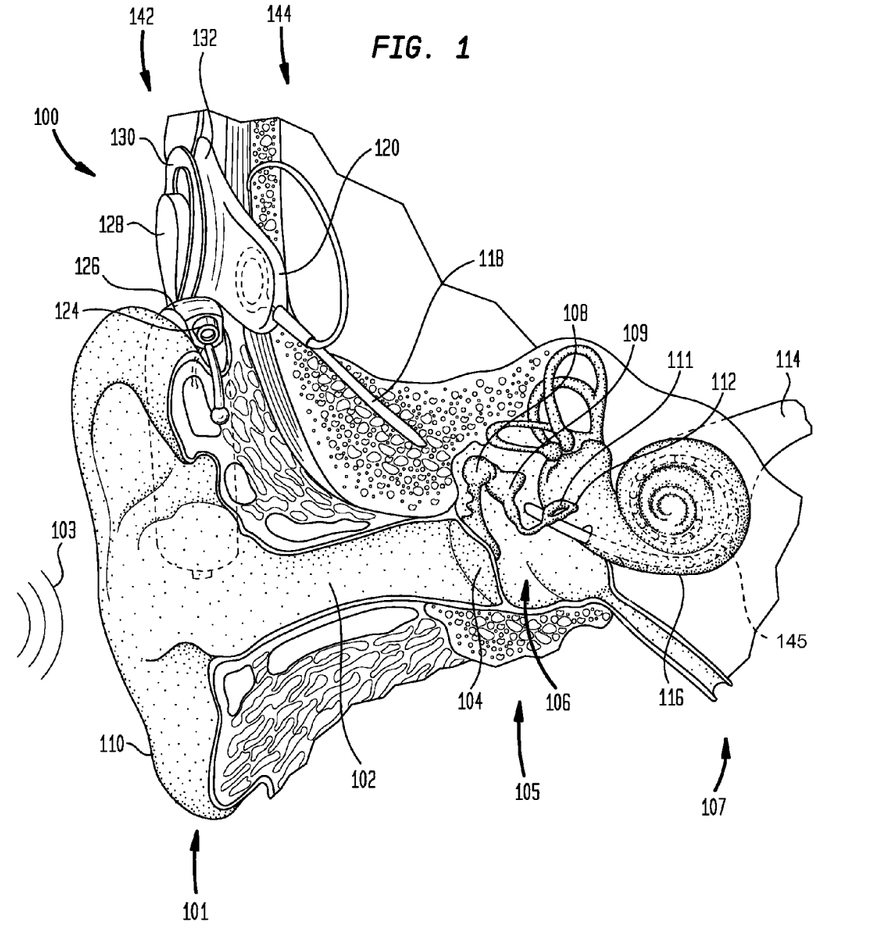
FIG. 1 is a perspective view of an implanted hearing prosthesis, namely a cochlear implant device, in which embodiments of the present invention may be advantageously implemented.

One medical device which can interoperate with a thermoelectric power source of the present invention is an auditory prosthesis, sometimes referred to as a hearing prosthesis. Auditory prostheses include hearing aids, auditory brain stimulators, and cochlear implants (also commonly referred to as cochlear prostheses, cochlear devices, cochlear implant devices, and the like; generally and collectively referred to as "cochlear implants" herein). Cochlear implants bypass the hair cells in the cochlea, directly delivering electrical stimulation to the auditory nerve fibers via an implanted electrode assembly. This enables the brain to perceive a hearing sensation resembling the natural hearing sensation normally delivered to the auditory nerve. FIG. 1 is a perspective view of a cochlear implant powered at least in part by a thermoelectric power source in accordance with the teachings of the present invention.

Referring to FIG. 1, the relevant components of outer ear 101, middle ear 105 and inner ear 107 are described next below. A fully functional outer ear 101 comprises an auricle 110 and an ear canal 102. An acoustic pressure or sound wave 103 is collected by auricle 110 and channelled into and through ear canal 102. Disposed across the distal end of ear cannel 102 is a tympanic membrane 104 which vibrates in response to acoustic wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify acoustic wave 103, causing oval window 112 to articulate, or vibrate. Such vibration sets up waves of fluid motion within cochlea 116. Such fluid motion, in turn, activates tiny hair cells (not shown) that line the inside of cochlea 116. Activation of the hair cells causes appropriate nerve impulses to be transferred through the spiral ganglion cells and auditory nerve 114 to the brain (not shown), where they are perceived as sound.

Cochlear implant system 100 comprises external component assembly 142 which is directly or indirectly attached to the body of the recipient, and an internal component assembly 144 which is temporarily or permanently implanted in the recipient. External assembly 142 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to the external coil. Speech processing unit 126 processes the output of audio pickup devices 124 that are positioned, in the depicted embodiment, by ear 110 of the recipient. Speech processing unit 126 generates coded signals, referred to herein as a stimulation data signals, which are provided to external transmitter unit 128 via a cable (not shown). Speech processing unit 126 is, in this illustration, constructed and arranged so that it can fit behind the outer ear 110. Alternative versions may be worn on the body or it may be possible to provide a fully implantable system which incorporates the speech processor and/or microphone into the implanted stimulator unit.

Internal components 144 comprise an internal receiver unit 132, a stimulator unit 120, and an electrode assembly 118. Internal receiver unit 132 comprises an internal transcutaneous transfer coil (not shown), and preferably, a magnet (also not shown) fixed relative to the internal coil. Internal receiver unit 132 and stimulator unit 120 are hermetically sealed within a biocompatible housing. The internal coil receives power and data from external coil 130, as noted above. A cable or lead of electrode assembly 118 extends from stimulator unit 120 to cochlea 116 and terminates in an array of electrodes 145. Signals generated by stimulator unit 120 are applied by electrodes 145 to cochlear 116, thereby stimulating the auditory nerve 114.

In one embodiment, external coil 130 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone moulding (not shown). In use, implantable receiver unit 132 may be positioned in a recess of the temporal bone adjacent ear 110 of the recipient.

Further details of a convention cochlear implant device may be found in U.S. Pat. Nos. 4,532,930, 6,537,200, 6,565,503, 6,575,894 and 6,697,674, which are hereby incorporated by reference herein in their entirety.

The thermoelectric device or devices of a thermoelectric power source of the present invention may be placed directly between the skin and bone of a recipient. In prosthetic hearing device applications such as that illustrated in FIG. 1, the thermoelectric device(s) may be located proximate to or at the mastoid area and positioned between the skin and skull. The thermoelectric power source of the present invention may be part of the housing that holds the implantable components for which it generates power, or it may be hermetically sealed in a separate housing electrically connected to the powered implantable unit.

In one embodiment, one thermal pole of the thermoelectric device(s) is positioned proximate to the sigmoid sinus of the recipient to provide a thermal coupling between the sigmoid sinus and that pole. The opposing thermal pole of the thermoelectric device(s) is positioned in the mastoid region behind the ear and near the surface of the recipient's body so as to provide a thermal coupling between the surface of the body and that thermal pole.

This positioning of the thermoelectric device(s) is advantageous because the skull or neck area of a recipient is rarely covered by heat-insulating clothing. Therefore, these areas normally have a temperature which is below the core temperature of the body. At the same time, the large blood vessels such as veins or arteries located in this area can provide a continuous heat energy supply to be converted into electric power by the thermoelectric device(s) in accordance with the present invention. For example, the external jugular vein, the anterior jugular vein, the transverse sinus, and the external carotid artery, are all blood vessels in this area of the body which can serve as a heat energy supply. By locating the thermoelectric device(s) of the present invention at these body areas, a significant and continual temperature difference may be maintained to allow practical use and efficient powering of an active implant such as the implantable components 144 of cochlear implant 100. Thus, a temperature difference which is constant on average over time can be reasonably anticipated so that electric power can be directly obtained by the thermoelectric device(s) without time limitation, stably over long durations, and without wear. In addition, the application of the present invention in the mastoid region 11 is advantageous because there is sufficient bone structure available directly underneath the surface of the skin and the bony structure which covers the sigmoid sinus is relatively easily accessible after a standard surgical procedure such as mastoidectomy.

Figure 2A:
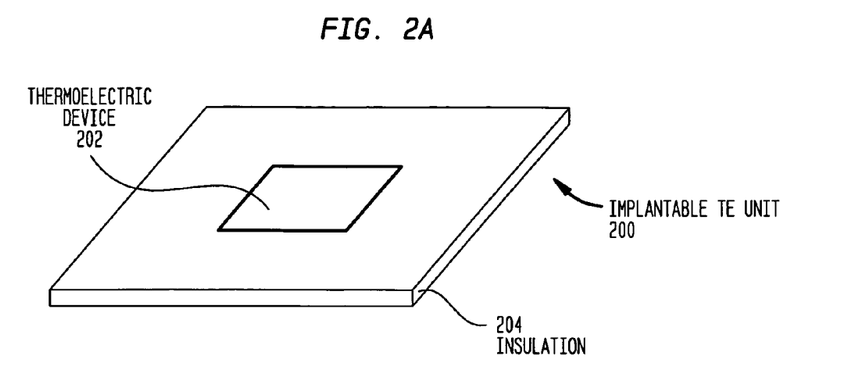
FIG. 2A is a simplified perspective view of an implantable thermoelectric unit in accordance with one embodiment of the present invention.
Figure 2B:
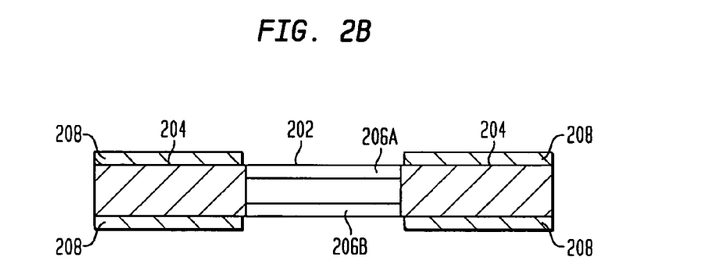
FIG. 2B is a cross-sectional view of one embodiment of the implantable thermoelectric unit illustrated in FIG. 2A.

FIG. 2A is a perspective view of an implantable thermoelectric (TE) unit in accordance with one embodiment of the present invention. FIG. 2B is a cross-sectional view of one embodiment of the implantable TE unit illustrated in FIG. 2A. As will be described in detail below, implantable thermoelectric unit 200 is constructed and arranged to be implanted between a recipient's skin and skull as described above, including locations outlined herein, when implemented to provide power to, for example, cochlear implant device 100.

In the embodiments shown in FIGS. 2A and 2B, implantable TE unit 200 comprises a single, somewhat planar, thermoelectric device 202. Disposed in the plane of thermoelectric device 202 is an insulator which preferably surrounds thermoelectric device 202. As shown in FIG. 2B, thermal poles 206A and 206B are disposed on opposing sides of thermoelectric device 202 to facilitate the thermal coupling of the thermoelectric device with its surrounding environment. It should be appreciated by one of ordinary skill in the art that the term "somewhat planar" would enable the thermoelectric device to be shaped in order to accommodate the shape of the skull, or another shape in the body where the thermoelectric device would be placed, in order to follow the contour of the body in the location of placement. In alternative embodiments the implantable thermoelectric unit is at least partially flexible.

At least one conducting layer 208 may coat all or part of the top and bottom surfaces of insulator 204. Although conducting layer(s) 208 are shown on opposing sides of insulator 204, it should be appreciated by one of ordinary skill in the art that such a conducting layer may be present on one surface of the insulator, or may be present on multiple surfaces, and in various configurations.

In the embodiment shown in FIG. 2B, a thermal pole 206 is exposed to the environment, such as the recipient's body in the application shown in FIG. 1, or to ambient air in other applications. It should also be appreciated that in alternative embodiments, a portion or all of either or both thermal poles 206 are also coated with conductive layer 208.

Figure 2C:
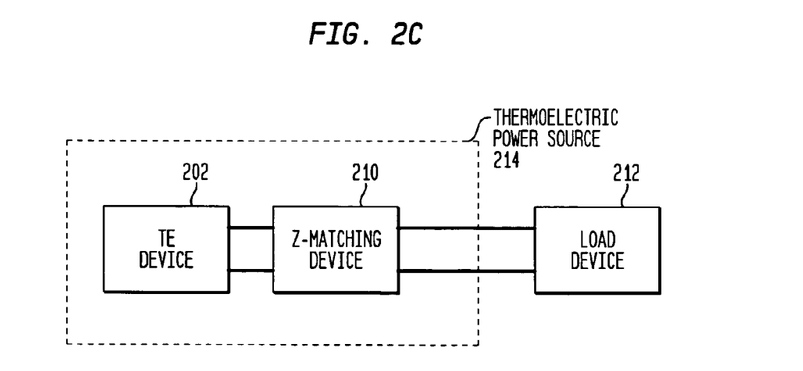
FIG. 2C is a simplified schematic block diagram of a thermoelectric power supply implementing an embodiment of the implantable thermoelectric unit illustrated in FIGS. 2A and 2B, in accordance with one embodiment of the present invention.

FIG. 2C is a schematic block diagram of one embodiment of the present invention. In this embodiment, a thermoelectric power source 214 comprises an embodiment of thermoelectric device 202 electrically coupled to a load device 212. Load device 212 may be, for example, stimulator unit 120 or another component of cochlear implant system 100 illustrated in FIG. 1.

The power output of a thermoelectric device 202 depends on the temperature across the device, commonly referred to as the thermal gradient. The thermal impedance of a thermoelectric device 202 depends on the electric current running through the device because of the Peltier effect. Decreasing the load resistance increases the current which in turn causes heat to be moved between the thermal poles 206 of device 202. This increases the equivalent thermal impedance of the thermoelectric device 202. Therefore, optimizing the power output of a given system comprising a thermoelectric device 202 and an electric load involves matching the thermal impedance by matching the output impedance of the thermoelectric device 202 with the input impedance of the electric load impedance. Thus, assuming there is a gradient in that direction, the larger the thermoelectric device 202, the more efficient the device may become.

In accordance with the teachings of the present invention, thermoelectric power source 214 further comprises an impedance matching device 210 constructed and arranged to match the output impedance of thermoelectric device 202 with the input impedance of load device 212. Matching the impedances maximizes the efficiency with which the thermoelectric device 202 operates, thereby maximizing the power generated by the device. The output impedance of thermoelectric device 202 is a function of a number of factors including the thermal impedance of the device and the configuration of the device, e.g., use of thermoelectric units having different output characteristics, in one thermoelectric device. Accordingly, to optimize the overall thermoelectric efficiency and maximize the power output of thermoelectric power source 214, impedance matching device 210 matches the load impedances according to the local adjacent thermal impedance.

Figure 3A:
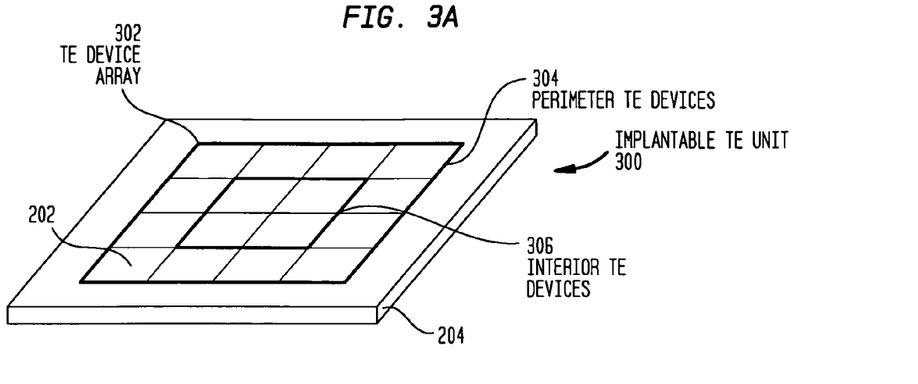
FIG. 3A is a simplified perspective view of an implantable thermoelectric unit in accordance with one embodiment of the present invention.
Figure 3B:
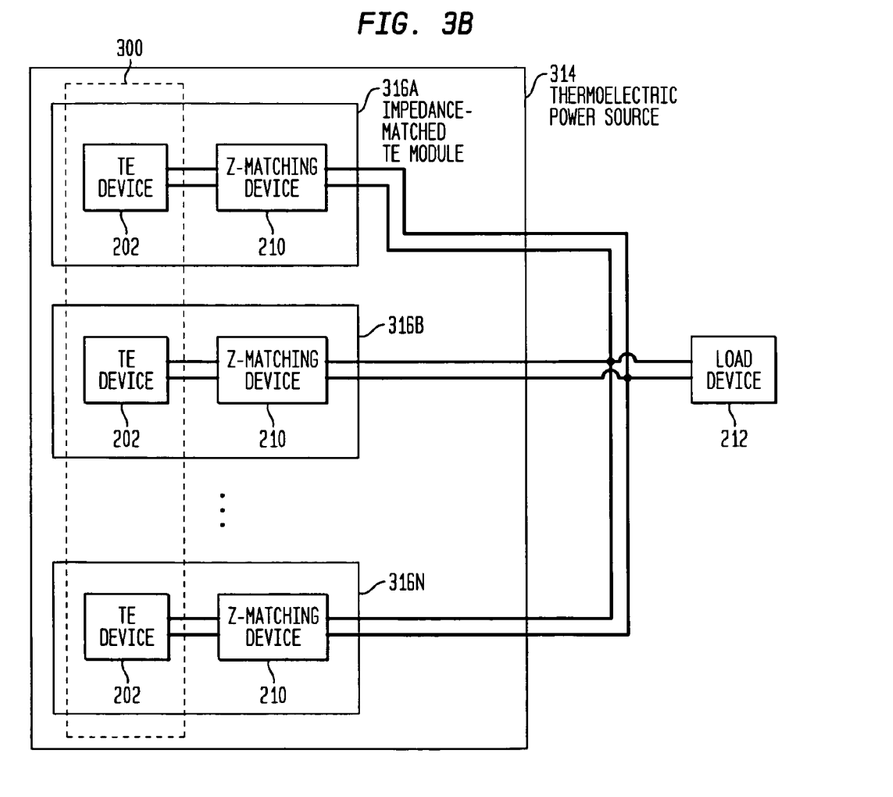
FIG. 3B is a schematic block diagram of a thermoelectric power supply implementing an embodiment of the implantable thermoelectric unit illustrated in FIG. 3A, in accordance with one embodiment of the present invention.

In another embodiment of the present invention, the implantable thermoelectric unit comprises an array of thermoelectric devices. FIG. 3A is a simplified perspective view of one embodiment of an implantable thermoelectric unit 300 having an array 302 of thermoelectric devices 202. FIG. 3B is a schematic block diagram of one embodiment of a thermoelectric power supply 314 implementing an embodiment of implantable thermoelectric unit 300. In FIG. 3B, three impedance-matched thermoelectric modules 316 are illustrated for clarity, although there are sixteen such modules 316 in this exemplary embodiment since there are sixteen thermoelectric devices 202 in array 302 illustrated in FIG. 3A.

Embodiments of implantable thermoelectric unit 300 may comprise any desired quantity of thermoelectric devices 202 arranged in an array 302 as shown in FIG. 3A. In some exemplary embodiments, the periphery of TE device array 302 is preferably surrounded by a thermal insulating material 204, as described above with reference to FIG. 2A. Such an insulator may reduce the edge effects without significantly increasing the volume of the device.

It should also be appreciated that, as noted above, the efficiency of an implanted thermoelectric unit increases as the size of the unit increases. Accordingly, in accordance with certain embodiments, implantable thermoelectric unit 300 is as large as possible to meet a particular power requirement while not adversely affecting the manufacturing, implantation or operation of the unit.

The inventors have observed that thermoelectric devices 202 located at different locations in thermoelectric array 302 may have different output impedances due to variations of factors including but not limited to a different thermal gradient. This results in variations in the output impedance of the individual thermoelectric devices 202, decreasing the efficiency of implantable TE unit 300.

In accordance with one embodiment of the present invention, thermoelectric power source 314 comprises a plurality of impedance matching circuits 210 each associated with, and electrically coupled to, one thermoelectric device 202. The combination of each TE device 202 and associated impedance matching device 210 is referred to herein as an impedance-matched TE module 316. In the embodiment shown in FIG. 3B, impedance-matched TE modules 316A-316N connected in parallel with each other to form thermoelectric power source 314, with the parallel arrangement of the impedance-matched TE modules connected to load device 212.

Advantageously, each impedance matching device 210 matches the output impedance of its associated thermoelectric device 202 with the input impedance of load device 212. As such, the specific thermal output impedance of each thermoelectric device 202 may be matched with the input impedance of load device 206. This enables thermoelectric power source 314 to compensate for variations in the local adjacent thermal impedance across the thermoelectric devices of array 302. Accordingly, the overall thermoelectric efficiency of implantable TE unit 300 is optimized thereby maximizing the power output of thermoelectric power source 314.

As one of ordinary skill in the art would appreciate, for an impedance matching device 210 of the present invention to match the output impedance of one or more thermoelectric devices 202, such impedance matching device 210 must be electrically coupled to the associated thermoelectric devices. It should also be appreciated that the selected electrical arrangement of thermoelectric devices 202 and impedance matching circuits 210 depends upon a variety of factors such as the desired efficiency of implantable thermoelectric unit 300, the output impedance of load 212, as well as the desired output current and voltage of thermoelectric power source 314. This is described in further detail below.

As one of ordinary skill in the art would appreciate, impedance matching circuits 210 may or may not be implemented in implantable TE unit 300, depending on a variety of factors such as the ultimate size of implantable TE unit 300, the intended implantation site of implantable TE unit 300; the size and complexity of impedance matching circuits 210, the relative manufacturing costs, the proximity of the impedance matching circuits 210 to the associated thermoelectric devices 202 should they be implemented in physically separate devices, among others. In the exemplary embodiment shown in FIG. 3B, implantable TE unit 300 is illustrated as a dashed box around thermoelectric devices 202 to schematically illustrate that impedance matching circuits 210 are not implemented in implantable TE unit 300.

The inventors have also observed that the impedance for optimal power transfer changes due to edge effects experienced by those thermoelectric devices 202 located along the periphery of TE device array 302. As a result, the thermal impedance between the perimeter thermoelectric elements and the surrounding environment is different than the thermal impedance between the interior thermoelectric elements and the surrounding environment.

In accordance with certain aspects of the present invention, therefore, the plurality of thermoelectric devices 202 which comprise TE device array 302 are defined herein to include perimeter TE devices 304 and at least one interior TE device 306. Perimeter TE devices 304 each have at least one edge which defines or is coincident with an edge of TE device array 302. In contrast, the edges of the at least one interior TE device 306 do not coincide with the edge of TE array 302. In the example shown in FIG. 3A, TE device array 302 comprises 16 thermoelectric devices 202 arranged in a 4×4 array. As such, TE device array 302 comprises 12 perimeter TE devices 304 and four interior TE devices 306, as shown.

Embodiments of the present invention take into consideration the fact that perimeter TE devices 304 have a different thermal gradient than interior TE devices 306 due to different edge effects of perimeter TE devices 304 and internal TE elements 306. Specifically, in accordance with certain embodiments, the implemented impedance-matched TE modules comprise a single impedance matching device 210 associated with a group of one or more thermoelectric devices 202.

Figure 3C:
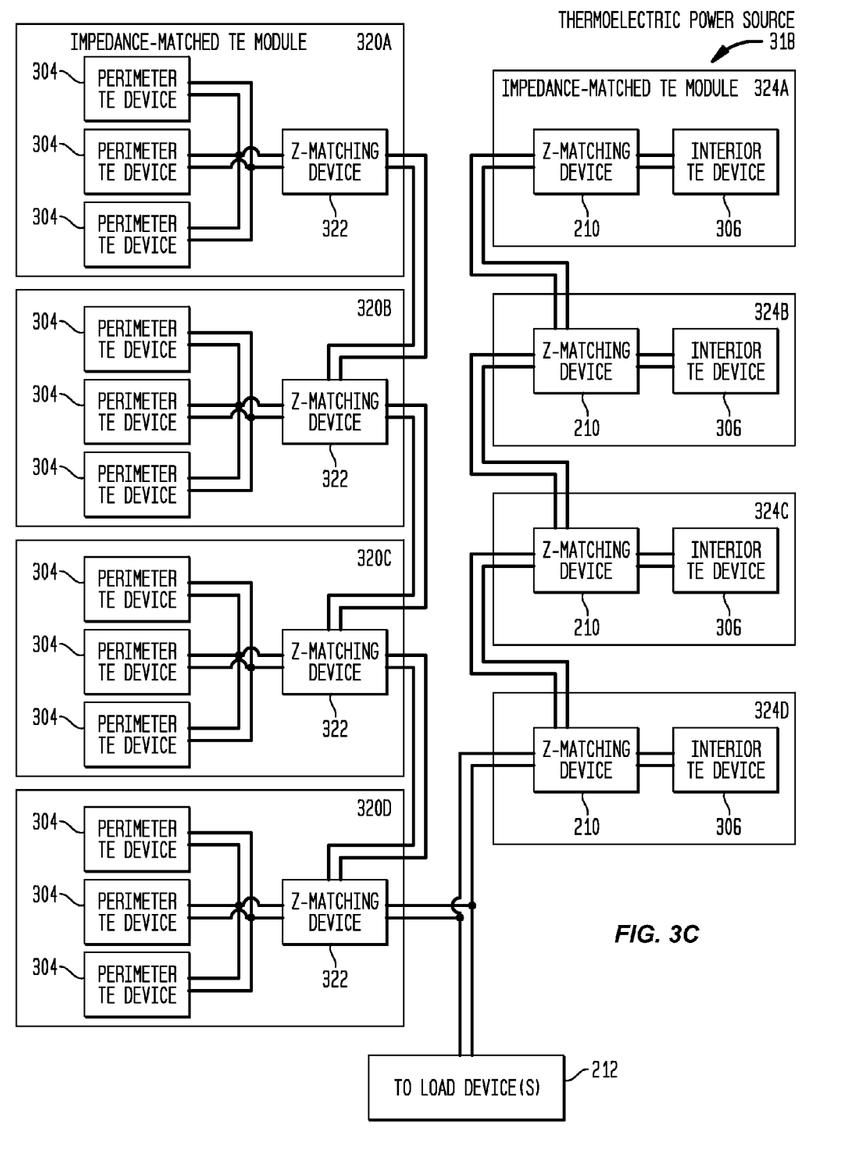
FIG. 3C is a schematic block diagram of a thermoelectric power source that comprises an implantable thermoelectric unit in accordance with one embodiment of the present invention.

FIG. 3C is a schematic block diagram on one embodiment of a thermoelectric power source 318 which comprises implantable TE unit 300. In this embodiment, three perimeter TE devices 304 are grouped together in a parallel circuit arrangement in each of four impedance-matched TE modules 320A-320D. Each impedance-matched TE modules 320 further comprises a single impedance matching circuit 322 which matches the impedance of the associated three perimeter TE devices 304 with the input impedance of load 212.

The four impedance-matched TE modules 320 are series-connected to each other, with the output of each impedance-matching device 322 provided as an input to the impedance-matching device 322 of a next impedance-matched TE module 320, and the output of the last impedance-matching device 322D provided as an input to load 212.

Similarly, each of the four interior TE devices 306 is connected to a dedicated impedance matching device 210, as described above. The resulting impedance-matched TE modules 324A-324D are series-connected to each other in a manner similar to the interconnection of impedance-matched TE modules 320. The output of the last impedance-matching device 324D provided as an input to load 212.

As shown in FIG. 3D, the series arrangement of impedance-matched TE modules 320 and the series arrangement of impedance-matched Te modules 324 are connected in parallel with each other prior to their connection to load device 212. Advantageously, the embodiment of the present invention illustrated in FIG. 3D enables those perimeter TE devices 304 which are subject to similar edge effects to be included in the same impedance-matched TE module 320. This enables the associated impedance-matching device 322 to optimally match the output impedances of the associated perimeter TE devices 304 with the input impedance of load device 212. A further advantage of the embodiment shown in FIG. 3D is that the output voltage of the perimeter TE devices 304 is substantially equivalent with the output voltage of the interior TE devices 306. As noted, one of the factors which may be considered in the selected arrangement of a thermoelectric power source of the present invention is the output voltage and current of the power source. The arrangement in FIG. 3D is one example of how such factors are considered in a design of such a thermoelectric power source 318.

As one of ordinary skill in the art would appreciate, there are many variations which may be implemented in alternative embodiments. For example, in the embodiment illustrated in FIG. 3A, TE device array 302 is a symmetrical, rectangular array with linear edges. It should be appreciated, however, that embodiments of a thermoelectric device array of the present invention need not be symmetrical and need not have linear edges. It should also be understood that the thermoelectric devices 202 included in thermoelectric device array 302 need not be the same type or size. Such variability, along with variability of the dimensions and geometry of the thermoelectric device array provide a designed with significant flexibility to create a thermoelectric device array which has a desired distribution of thermal impedances. In embodiments in which different types of thermoelectric modules are utilized, each group of thermoelectric modules 302 which are associated with an impedance matching device 210 are of the same type since such common thermoelectric devices have approximately the same output impedance.

As one of ordinary skill in the art would appreciate, each impedance matching device such as those described herein, can be set by a designed or user of the power source or by a user of a load device 212 which is being powered by the thermoelectric power source.

Figure 4:
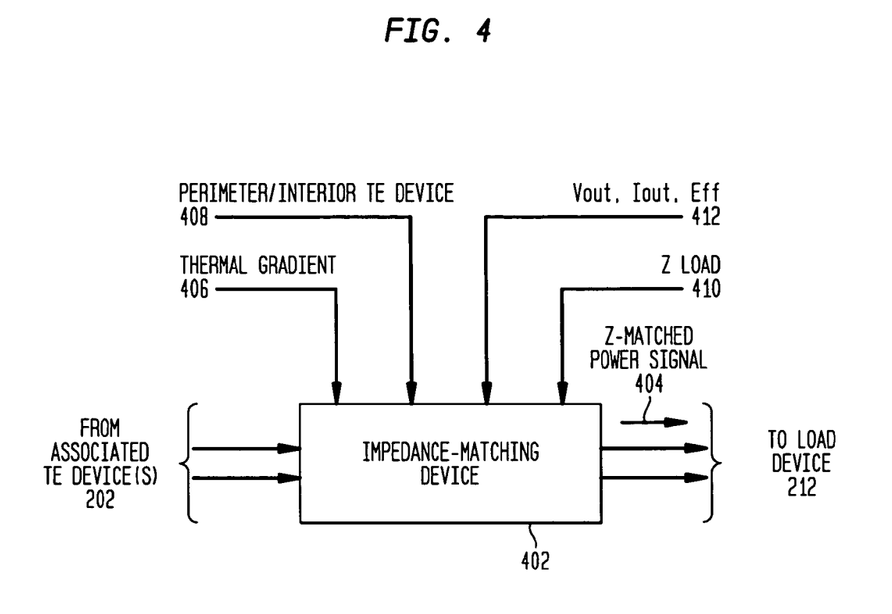
FIG. 4 is a schematic block diagram of an alternative embodiment of an impedance matching device of the present invention.

In one alternative embodiment, the impedance matching device is constructed and arranged to adjust the output impedance of its associated thermoelectric device(s) based on a combination of one or more of the above and other factors. An exemplary embodiment of such an impedance matching device 402 is illustrated in FIG. 4. Impedance matching device 402 is electrically coupled to one or more thermoelectric devices 202 and provides the impedance-matched power signal 404 to one or more load devices 212 to which the device 402 is connected.

In the embodiment shown in FIG. 4, impedance matching device 402 adjusts the impedance of the associated thermoelectric device(s) 202 based on the thermal gradient 406 of the device(s), an indication 408 of whether the associated device (s) is/are a perimeter TE device(s) 304 or interior TE device(s) 306, the input impedance 410 of load 212, and other settings 412 such as the desired efficiency of the implemented implantable thermoelectric unit, the desired output current and voltage of thermoelectric power source, and so on.

As one of ordinary skill in the art would appreciate, additional or alternative factors may be considered by impedance matching device 402 to match the output impedance of the associated TE device(s) 202 with the input impedance of load device(s) 212. For example, in the embodiment described above, indication 408 identifies the associated device(s) 202 as either perimeter TE devices 304 or interior TE device(s) 306. However, it should be understood that other indications representing a characterization of the associated TE devices based on expected edge effects or other conditions which may alter the thermal efficiency of the associated devices may be used. It should also be appreciated that the design and manufacture of an impedance matching device 402 that performs the functions and operations of the present invention is well-known to those of ordinary skill in the art.

It should also be appreciated that certain of the above factors may change more readily than other factors. For example, in the above exemplary embodiment, the thermal gradient 406 of the associated TE device(s) 202 will likely change over time, while the type 408 of the device will not. Similarly, the impedance of load device(s) 212 may change either due to a change in the type of load or due to a change in the load device itself, such as due to a depletion of the stored energy in an energy storage device. Impedance-matching device 402 would be configured to periodically receive or query for such information to provide continued optimal performance of the implementing thermoelectric power source.

Figure 5:
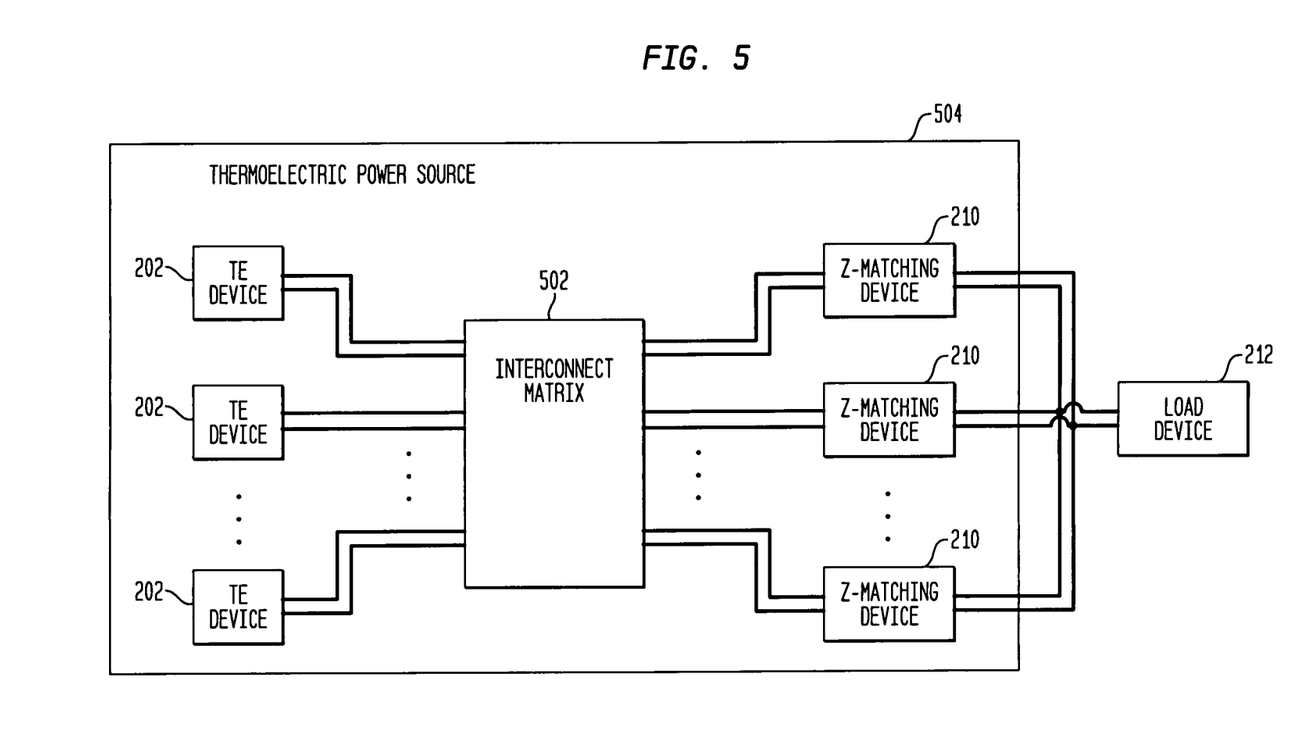
FIG. 5 is an alternative embodiment of a thermoelectric power source of the present invention.

FIG. 5 is an alternative embodiment of a thermoelectric power source 504. In this embodiment there is no predetermined association between thermoelectric devices 202 and impedance matching devices. Rather, thermoelectric power source 504 comprises an interconnect matrix 502 that connects groups of one or more thermoelectric devices 202 with an impedance matching device 210. The outputs of the impedance matching devices 210 are then combined and provided to load device 212.

Interconnect matrix 502 connects thermoelectric devices 202 with impedance matching devices 210 based on the above factors. In such embodiments, interconnect matrix 502 includes or is operatively coupled to a microcontroller, processor or the like that implements logic to interconnect devices 202 and 210 based on selected factors such as those noted above. In addition or alternatively, interconnect matrix 502 may be manually configured prior to real-time operations. It should be understood that the design and manufacture of an interconnect matrix in accordance with the teachings of the present invention is considered to be well-known in the art and, therefore, is not described further herein.

Figure 6:
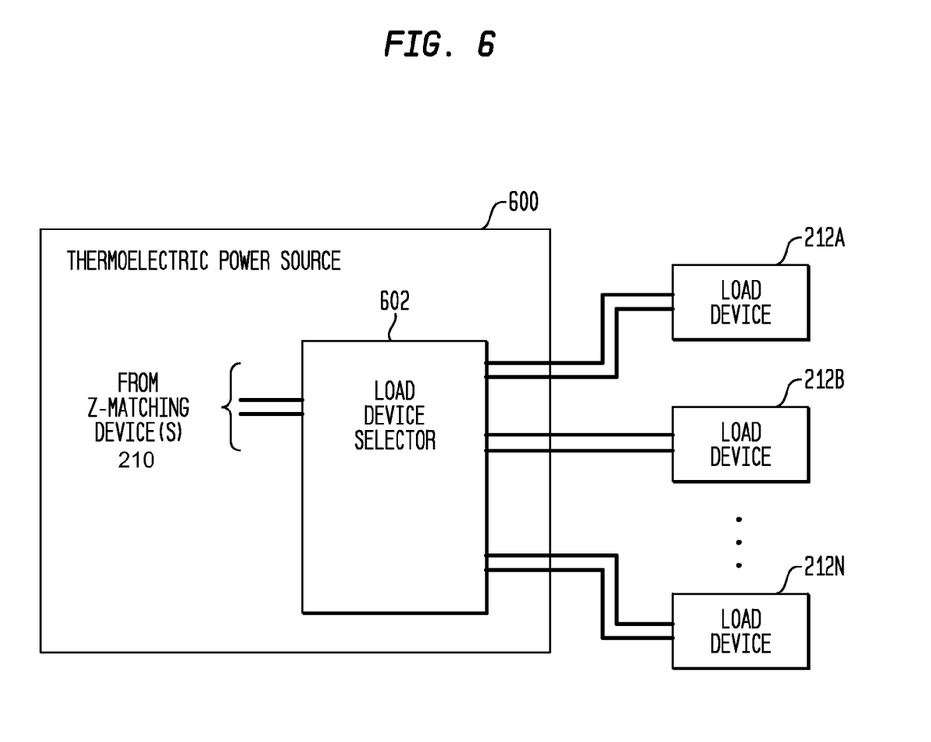
FIG. 6 is a schematic block diagram of a thermoelectric power source in accordance with one embodiment of the present invention.

FIG. 6 is a schematic block diagram of another embodiment of a thermoelectric power source of the present invention. In certain applications, the thermoelectric power source of the present invention is constructed and arranged to deliver power to a selected one or more load devices 212. In the embodiment shown in FIG. 6, a thermoelectric power source 600 may be electrically coupled to one or more load devices 212A-212N. Each load device 212 may be, as noted above, a power-consuming device or an energy-storage device.

Thermoelectric power source 600 comprises one or more thermoelectric devices 202 and impedance matching devices 210 such as, or analogous to, the embodiments described above. Thermoelectric power source 600 further comprises a load device selector 602 which selectively couples the output leads from the one or more impedance matching devices 210 of thermoelectric power source 600 to one or more load devices 212.

For example, in one embodiment, the generated power may be provided directly to a power-consuming device such as a rechargeable energy storage device to continually provide back-up power to prevent undue deep discharge of the storage device. In other embodiments, when the power-consuming device and/or an internal energy storage device no longer require power, load selector 602 disconnects thermoelectric power source 600 from such load devices and connects it to an external energy storage device. As one of ordinary skill in the art would appreciate, load selector 602 may be configured to connect thermoelectric power source 600 directly or indirectly to any combination of load devices in any sequence appropriate for the particular application. It should also be appreciated that load device selector 602 may be configured to include the capability to implement the requisite logic to perform such interconnect operations. Such logic maybe including in an ASIC, microcontroller, processor-based software, hardware or the like contained in or operationally coupled to load selector 602.

In the particular application of cochlear implant 100 illustrated in FIG. 1, the power generated by embodiments of the thermoelectric power source 600 may directly power to stimulator unit 120. In addition, excess power of the power supply may power the external components 142. In some prosthetic hearing devices, the microphone and speech processor may be positioned in the implantable unit; that is, the auditory prosthesis may be a totally implantable device, including an implantable rechargeable battery (any chemistry). In such an application, thermoelectric power source 600 may also supply power to all implanted components.

Because thermoelectric devices are relatively thin, to provide an implantable thermoelectric unit which comprises an array of a large quantity of thermoelectric devices may result in the implantable thermoelectric unit having dimensions which adversely affect the manufacture, implantation or operation of the unit.

Figure 7:
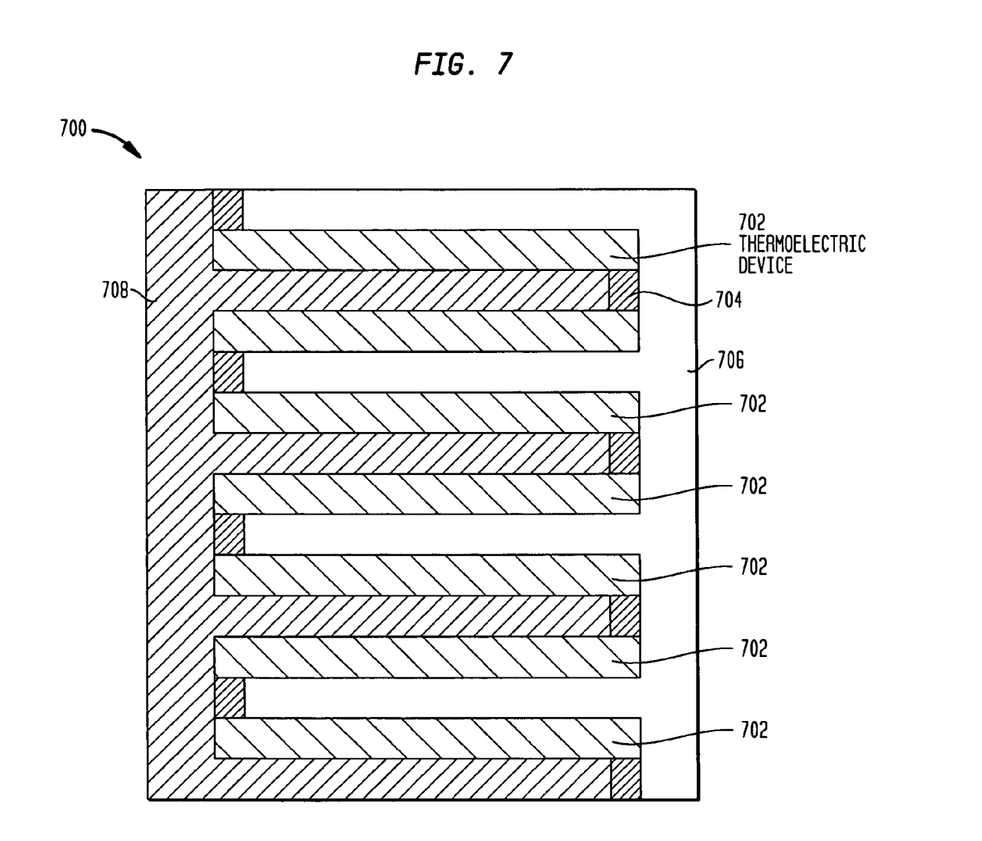
FIG. 7 is a schematic block diagram of a implantable thermoelectric unit in accordance with one embodiment of the present invention.

FIG. 7 is a cross-sectional view of an implantable thermoelectric unit 700 in accordance with an alternative embodiment of the present invention. In this embodiment, a plurality of thermoelectric devices 702 is retained in a three-dimensional structure to minimize the volume or surface area of the device. As shown in this cross-sectional view, structure 700 comprises a plurality of thermoelectric devices 702 positioned between a two thermal poles 706 and 708. Each thermal pole 706, 708 has a plurality of extensions or heat conductors, possibly heat pipes which extend across device 700. Such heat conductors transfer heat across the long surface of the thermoelectric devices 702 and terminate with an insulating buffer 704. In this configuration, heat which is conducted through one thermal pole 706, 708 through thermoelectric devices 702 and into the heat conductors of the opposing thermal pole 706, 708. This facilitates the transfer of heat between the thermal poles 706, 708.

The embodiment of the implantable thermoelectric unit 700 illustrated in FIG. 7 has a reduced surface area and greater thickness that the implantable units described above. Implantable thermoelectric unit 700 may be suitable for implantation in certain locations of the recipient not otherwise suitable for the configurations described elsewhere herein.

Further features of the present invention are described in U.S. Provisional Patent No. 60/586,718 entitled, "Optimization of Thermoelectric Devices For Powering Active Implantable Medical Devices," filed Jul. 12, 2004, which is hereby incorporated by reference herein in its entirety.

It will be appreciated by persons skilled in the art that numerous variations and/or modifications may be made to the invention as shown in the specific embodiments without departing from the spirit or scope of the invention as broadly described. For example, in an embodiment of the present invention, an insulator or insulating layer or layers may be constructed around the thermoelectric device to increase, and in some embodiments, to maximize, the temperature difference across the thermoelectric device. The temperature difference across the thermoelectric device allows the thermoelectric device to operate at a high efficiency, thus allowing more electrical power to be produced. Furthermore, the insulator or insulating layer or layers have the effect of stabilizing the power output of the thermoelectric device over a wider range of load resistances, as opposed to a non-insulated thermoelectric device. As another example, anisotropic materials, such as graphite, may be used to increase the heat flux horizontally across the thermoelectric devices and to impede the heat transfer across the thermoelectric device, thus increasing the power output of the device by allowing the thermoelectric device to transduce more of the energy that is in the insulator region. In a further example, it may also be beneficial to place a thermal conductor, such as copper or other suitable material, on the surface of the insulator to increase the amount of heat transferring through the thermoelectric devices. This also reduces the waste heat and may decrease the required width of the insulating material. As another example, it should be appreciated that although embodiments of the present invention are described herein in connection with implantable hearing devices, the same or other embodiments of the present invention may be implemented in other prosthetic devices as well. Examples of such devices include, but are not limited to, other sensory prosthetic devices, neural prosthetic devices, and functional electrical stimulation (FES) systems. Other suitable embodiments and modifications may be discerned from U.S. Pat. No. 6,131,581, the entire contents and disclosure of which is hereby incorporated by reference. The present embodiments are, therefore, to be considered in all respects as illustrative and not restrictive.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

What is claimed is:

1. A thermoelectric power source for generating power for use by at least one load device comprising:
    a thermoelectric (TE) device array configured to be electrically coupled to said at least one load device, said TE device array comprising:
        a plurality of perimeter TE devices each having at least one edge which is coincident with an edge of said TE device array; and
        at least one interior TE device the edges of which do not coincide with an edge of said TE device array; and
    at least one first impedance matching device:
        constructed and arranged to match an output impedance of one or more of said perimeter TE devices with an input impedance of said load device, and
        electrically coupled to the output of one or more of said perimeter TE devices; and
    at least one second impedance matching device:
        constructed and arranged to match an output impedance of one or more said interior TE devices with an input impedance of said load device, and
        electrically coupled to the output of one or more of said interior TE devices.

2. The power source of claim 1, wherein
said at least one load device comprises one of an energy storage device and a power-consuming device.

3. The power source of claim 2, wherein
said energy storage device comprises one or more of:
    at least one rechargeable battery; and
    at least one capacitor.

4. The power source of claim 2, wherein
said load device comprises one or more components of an active implantable medical device (AIMD).

5. The power source of claim 4, wherein said AIMD comprises:
at least a portion of an auditory prosthesis.

6. The power source of claim 5,
wherein said auditory prosthesis comprises:
a cochlear implant device.

7. The power source of claim 1, wherein
said thermoelectric device array is constructed and arranged to be implanted between a recipient's skin and bone.

8. The power source of claim 7, wherein
said thermoelectric device array is constructed and arranged to be implanted proximate to a recipient's mastoid area.

9. The power source of claim 8,
wherein said thermoelectric power source comprises a first thermal pole and an opposing second thermal pole, and
wherein said first thermal pole and second thermal pole are configured to be positioned proximate to a recipient's sigmoid sinus
to thermally couple the sigmoid sinus and said first thermal pole, and
to thermally couple a surface of the recipient's body and said second thermal pole.

10. The power source of claim 1, wherein
said thermoelectric power source further comprises:
an insulator disposed in a plane of said TE device array surrounding a periphery of said TE device array.

11. The power source of claim 10, wherein
said thermoelectric power source further comprises:
at least one conducting layer disposed over at least a portion of at least one of a top and bottom surface of said insulator.

12. The power source of claim 1, wherein
said impedance matching device matches said impedances according to a local adjacent thermal impedance.

13. The power source of claim 1, wherein
said TE device array has linear edges.

14. The power source of claim 1, wherein
said TE device array is symmetrical.

15. The power source of claim 1, wherein
said electrical connection of said TE devices and said impedance matching devices affects one or more of:
an efficiency of said thermoelectric power source;
an output impedance of said at least one load device;
an output current of said thermoelectric power source; and
an output voltage of said thermoelectric power source.

16. An active implantable medical device comprising:
at least one load device; and
a thermoelectric (TE) power source for generating power for use by said at least one load device comprising:
an array of TE devices configured to be electrically coupled to said at least one load device, said TE device array comprising:
a plurality of perimeter TE devices each having at least one edge which is coincident with an edge of said TE device array; and
at least one interior TE device the edges of which do not coincide with an edge of said TE device array; and
at least one first impedance matching device each electrically coupled to at least one of said perimeter TE devices and configured to match an output impedance of said at least one perimeter TE device with an input impedance of said load device; and
at least one second impedance matching device each electrically coupled to one or more of said at least one interior TE device, and configured to match an output impedance of said one or more interior TE devices with an input impedance of said load device.

17. The medical device of claim 16, wherein
said thermoelectric power source further comprises:
an insulator disposed in a plane of said TE device array surrounding a periphery of said TE device array.

18. The medical device of claim 16, wherein
said at least one load device comprises:
a power-consuming implantable component.

19. The medical device of claim 16, wherein
said at least one load device comprises:
an energy storage device coupled to a power-consuming implantable component.

20. The medical device of claim 18, wherein
said active implantable medical device is a cochlear implant device.

21. The medical device of claim 20, wherein
said implantable thermoelectric unit is constructed and arranged to be implanted between a recipient's skin and bone proximate to a recipient's mastoid area.

22. The medical device of claim 16, further comprising:
a plurality of impedance-matched TE modules, each comprising one of said impedance matching devices electrically coupled to one or more of said TE devices of said TE device array.

23. The medical device of claim 22, wherein
said impedance-matched TE modules are connected in parallel with each other.

24. The medical device of claim 22, wherein
said electrical coupling of said TE devices and said impedance matching devices affects one or more of:
an efficiency of said thermoelectric power source;
an output impedance of said at least one load device;
an output current of said thermoelectric power source; and
an output voltage of said thermoelectric power source.

25. A thermoelectric (TE) power supply for electrically coupling to a load, the TE power supply comprising:
an array of TE devices, said array comprising:
a plurality of perimeter TE devices each having at least one edge that is coincident with an edge of said array; and
at least one interior TE device the edges of which do not coincide with an edge of said array; and
at least one first impedance matching device:
constructed and arranged to match an output impedance of one or more of said perimeter TE devices with an input impedance of said load;
electrically coupled at an input to at least one of said perimeter TE devices, and
electrically coupleable at an output of one or more of said perimeter TE devices to said load; and
at least one second impedance matching device:
constructed and arranged to match an output impedance of one or more of said interior TE devices with an input impedance of said load;
electrically coupled at an input to at least one of said interior TE devices, and
electrically coupleable at an output of one or more of said interior TE devices to said load.

26. The power supply of claim 25, wherein
said load comprises:
  a power-consuming implantable component.

27. The power supply of claim 25, wherein
said load comprises:
  an energy storage device coupled to a power-consuming implantable component.

28. The power supply of claim 26, wherein
said power-consuming implantable component is a cochlear implant device.

29. The power supply of claim 26, wherein
said implantable component is constructed and arranged to be implanted between a recipient's skin and bone proximate to a recipient's mastoid area.

30. The power supply of claim 25, wherein
said electrical connection of said TE devices and said impedance matching devices affects one or more of:
  an efficiency of said thermoelectric power supply;
  an output impedance of said at least one load;
  an output current of said thermoelectric power supply; and
  an output voltage of said thermoelectric power supply.

* * * * *